US011135566B2

(12) United States Patent
Han et al.

(10) Patent No.: US 11,135,566 B2
(45) Date of Patent: Oct. 5, 2021

(54) POROUS FIBER AND ADSORPTION COLUMN

(71) Applicant: Toray Industries, Inc., Tokyo (JP)

(72) Inventors: Aishan Han, Otsu (JP); Hiroaki Fujieda, Otsu (JP); Yoshiyuki Ueno, Otsu (JP)

(73) Assignee: Toray Industries, Inc.

( * ) Notice: Subject to any disclaimer, the term of this patent is extended or adjusted under 35 U.S.C. 154(b) by 157 days.

(21) Appl. No.: 16/496,633

(22) PCT Filed: Mar. 23, 2018

(86) PCT No.: PCT/JP2018/011722
§ 371 (c)(1),
(2) Date: Sep. 23, 2019

(87) PCT Pub. No.: WO2018/186210
PCT Pub. Date: Oct. 11, 2018

(65) Prior Publication Data
US 2020/0376465 A1 Dec. 3, 2020

(30) Foreign Application Priority Data

Apr. 4, 2017 (JP) ............................. JP2017-074185

(51) Int. Cl.
| *A61M 1/16* | (2006.01) |
| *B01D 15/18* | (2006.01) |
| *B01J 20/20* | (2006.01) |
| *B01J 20/28* | (2006.01) |
| *B01J 20/285* | (2006.01) |
| *D01F 1/10* | (2006.01) |
| *D01F 6/16* | (2006.01) |
| *D01F 8/10* | (2006.01) |
| *B01J 20/02* | (2006.01) |

(Continued)

(52) U.S. Cl.
CPC .......... *B01J 20/285* (2013.01); *A61M 1/1621* (2014.02); *B01D 15/1871* (2013.01); *B01J 20/0207* (2013.01); *B01J 20/0277* (2013.01); *B01J 20/06* (2013.01); *B01J 20/20* (2013.01); *B01J 20/205* (2013.01); *B01J 20/261* (2013.01); *B01J 20/28004* (2013.01); *B01J 20/2808* (2013.01); *B01J 20/28026* (2013.01); *B01J 20/28052* (2013.01); *B01J 20/28059* (2013.01); *B01J 20/28083* (2013.01); *B01J 20/28085* (2013.01); *D01F 1/10* (2013.01); *D01F 6/16* (2013.01); *D01F 8/10* (2013.01); *B01J 2220/46* (2013.01); *D10B 2401/10* (2013.01); *D10B 2509/00* (2013.01)

(58) Field of Classification Search
CPC ........ B01J 20/20; B01J 20/205; B01J 20/324; B01J 20/262; B01J 20/3212; B01J 20/28023; B01J 20/28026; B01J 20/28028; B01J 20/28078; B01J 20/2808; B01J 20/28083; B01J 20/28085; B01J 20/28004; B01J 28/28011; B01J 28/28054; B01J 28/3293; B01J 20/0207; B01J 20/0277; B01J 20/06; B01J 20/261; B01J 28/28026; B01J 20/28052; B01J 20/28059; B01J 20/285; B01J 2220/46; D01F 8/16; D01F 8/18; D01F 1/02; D01F 1/10; D01F 6/16; D01F 8/10; A61M 1/1621; B01D 15/1871; D10B 2401/10; D10B 2509/00

See application file for complete search history.

(56) References Cited

U.S. PATENT DOCUMENTS 4,164,437 A * 8/1979 Henne ................... B01D 69/147
156/167
4,302,509 A * 11/1981 Coplan ...................... D01D 5/34
428/372

(Continued)

FOREIGN PATENT DOCUMENTS

| JP | 03260170 A | 11/1991 |
| JP | 0693516 A | 4/1994 |

(Continued)

OTHER PUBLICATIONS

Nguyen et al. Porous core/sheath composite nanofibers fabricated by coaxial electrospinning as a potential mat for drug release system. International Journal of Pharmaceutics 439 (2012) 296-306. (Year: 2012).*

(Continued)

*Primary Examiner* — Benjamin L Lebron
(74) *Attorney, Agent, or Firm* — RatnerPrestia

(57) ABSTRACT

The present invention provides: a porous fiber that exhibits both improved adsorption capacity, and suppressed exposure and detachment of particulates; an adsorption column filled with said porous fiber; and a blood purification system in which an adsorption column is connected to a water removal column. The porous fiber according to the present invention has a three-dimensional pore structure formed by a solid fiber, and satisfies all of the following conditions. (1) The porous fiber has particulates having a diameter of not more than 200 μm, and the percentage of area occupied by said particulates having a diameter of not more than 200 μm in a horizontal cross section of the three-dimensional pore structure is at least 3.0%. (2) The porous fiber does not contain said particulates having a diameter of not more than 200 μm in the region within 1.0 μm in the depth direction from the outermost surface.

14 Claims, No Drawings

(51) Int. Cl.
*B01J 20/06* (2006.01)
*B01J 20/26* (2006.01)

(56) References Cited

U.S. PATENT DOCUMENTS

| | | | | |
|---|---|---|---|---|
| 5,019,445 | A * | 5/1991 | Sternlieb | D01F 1/04 |
| | | | | 428/221 |
| 7,935,418 | B2 * | 5/2011 | Koops | B01D 69/08 |
| | | | | 428/364 |
| 8,133,308 | B2 * | 3/2012 | Lively | B01D 53/0438 |
| | | | | 96/154 |
| 8,658,041 | B2 * | 2/2014 | Koros | B01J 20/28028 |
| | | | | 210/660 |
| 10,525,399 | B2 * | 1/2020 | Coignet | B01D 53/0407 |
| 2001/0009756 | A1 * | 7/2001 | Hei | A61L 2/0082 |
| | | | | 435/2 |
| 2003/0196549 | A1 * | 10/2003 | Rohrbach | B01D 53/81 |
| | | | | 95/90 |
| 2008/0053891 | A1 | 3/2008 | Koops et al. | |
| 2009/0156075 | A1 * | 6/2009 | Rollin, Jr. | D01F 8/16 |
| | | | | 442/199 |
| 2010/0029161 | A1 * | 2/2010 | Pourdeyhimi | D04H 3/11 |
| | | | | 442/329 |
| 2010/0313755 | A1 * | 12/2010 | Koros | B01J 20/3268 |
| | | | | 95/135 |
| 2012/0276360 | A1 * | 11/2012 | Kwak | D01F 8/16 |
| | | | | 428/221 |
| 2013/0196405 | A1 * | 8/2013 | Singh | D01D 5/0007 |
| | | | | 435/182 |

FOREIGN PATENT DOCUMENTS

| | | |
|---|---|---|
| JP | 2007046178 A | 2/2007 |
| JP | 2008510083 A | 4/2008 |
| JP | 2010227757 A | 10/2010 |
| JP | 2014189937 A | 10/2014 |

OTHER PUBLICATIONS

International Search Report and Written Opinion for International Application No. PCT/JP2018/011722 dated Jun. 12, 2018, 6 pages.

* cited by examiner

POROUS FIBER AND ADSORPTION COLUMN

CROSS REFERENCE TO RELATED APPLICATIONS

This is the U.S. National Phase application of PCT/JP2018/011722, filed Mar. 23, 2018, which claims priority to Japanese Patent Application No. 2017-074185, filed Apr. 4, 2017, the disclosures of these applications being incorporated herein by reference in their entirety for all purposes.

FIELD OF THE INVENTION

The present invention relates to a porous fiber. The present invention also relates to an adsorption column including the porous fiber packed into the adsorption column. Further, the present invention relates to a blood purification system including the adsorption column and a water removal column, in which the adsorption column and the water removal column are connected.

BACKGROUND OF THE INVENTION

Conventionally, a granular material has been used as an adsorbent for the purpose of adsorbing and removing a substance to be removed in fluid that is to be treated. Because the granular material itself has poor handleability, it has been used with being supported on a fiber and the like. In this case, to improve the adsorption capability of the granular material for a substance to be removed, the distance between the fluid that is to be treated and the granular material needs to be as short as possible. However, when the fluid that is to be treated and the granular material are in direct contact, the granular material may be damaged or may flow out from the fiber or the like supporting the granular material by the flow stress generated when the fluid that is to be treated flows. Further, when the fluid that is to be treated is blood, the direct contact between the granular material and hemocytes may lead to unintended activation of blood. Thus, important are the position of the granular material in the fiber and the design of the flow path to efficiently lead the substance to be removed in the fluid that is to be treated to the granular material in the fiber.

For example, Patent Document 1 discloses the invention related to a fiber for clothing in which a granular material is contained in a core and a sheath.

Similarly, Patent Document 2 defines that a sheath also contains the granular material. There is a description that the core is composed of only the granular material.

Meanwhile, the invention in which the fluid that is to be treated and the granular material are not in direct contact is also disclosed. Patent Document 3 discloses the invention for a separation membrane containing a granular material for water treatment use.

Patent Documents

Patent Document 1: Japanese Patent Laid-open Publication No. 2014-189937
Patent Document 2: Japanese Translation of PCT International Application Publication No. 2008-510083
Patent Document 3: Japanese Patent Laid-open Publication No. 2010-227757

SUMMARY OF THE INVENTION

However, for the fiber for clothing in which a granular material is contained in a core and a sheath, as described in Patent Document 1, the point that the exposure of the granular material on the fiber surface should be suppressed, and the method of suppression are not disclosed.

For the structure in which a sheath also contains a granular material and the core is composed of only a granular material, as described in Patent Document 2, the granular material may peel off from the yarn section when the fiber is broken by external pressure. Similarly, the point on the suppression of the exposure of the granular material on the fiber surface is not disclosed.

In the case where the layer containing the adsorbent has a spherical structure, as described in Patent Document 3, there is a concern that controlling the flow path of the fluid that is to be treated is difficult, and the variation of the flow path diameter may become large. There is also a concern that the supportability for the granular material may be lowered in particular between the spherical structures.

As described above, in the conventionally proposed fibers containing a granular material, in order to increase capability, the main focus is on improving the addition rate of a granular material and imparting mechanical strength of the fiber, and there is no description on the method for suppressing the exposure of the granular material on the fiber surface and peeling off from the section.

Thus, the present invention provides a porous fiber in which the exposure and peeling off of a granular material are suppressed, and simultaneously adsorption capability is increased. The present invention provides an adsorption column including the porous fiber packed into the adsorption column. Further, the present invention provides a blood purification system including the adsorption column and a water removal column, in which the adsorption column and the water removal column are connected.

As a result of intensive studies to solve the above-mentioned problems, the present inventors found that a highly safe porous fiber having suppressed exposure of a granular material and excellent adsorption capability can be obtained.

Further, the porous fiber of the present invention is capable of adsorbing and removing a high molecular weight compound that is not adsorbed or removed by the adsorption capability of the internally contained granular material.

That is, the porous fiber of the present invention has the following structure.

A porous fiber including a three-dimensional pore structure formed by a fiber having a solid shape, wherein the porous fiber satisfies all requirements below:

(1) having a granular material having a particle diameter of 200 μm or less, and having an area occupancy rate of the granular material having a particle diameter of 200 μm or less, in a cross section of the three-dimensional pore structure, of 3.0% or more; and (2) not having the granular material having a particle diameter of 200 μm or less in a region within 1.0 μm in a depth direction from an outermost surface.

According to the present invention, a porous fiber in which the exposure and peeling off of a granular material are suppressed, and simultaneously adsorption capability is increased can be obtained. An adsorption column including the porous fiber packed into the adsorption column can be obtained. Further, a blood purification system including the adsorption column and a water removal column, wherein the adsorption column and the water removal column are connected can be obtained.

DETAILED DESCRIPTION OF EMBODIMENTS OF THE INVENTION

The porous fiber, the adsorption column, and the blood purification system of the present invention will be specifically described below.

The porous fiber of the present invention includes a three-dimensional pore structure formed by a fiber having a solid shape, and satisfies all requirements below:

(1) having a granular material having a particle diameter of 200 μm or less, and having an area occupancy rate of the granular material having a particle diameter of 200 μm or less, in a cross section of the three-dimensional pore structure, of 3.0% or more; and (2) not having the granular material having a particle diameter of 200 μm or less in a region within 1.0 μm in a depth direction from an outermost surface.

The fiber having a solid shape in the present invention means a solid yarn having no hollow part.

In the present invention, the porous fiber has a three-dimensional pore structure. The three-dimensional pore structure refers to a structure that is three-dimensionally expanded and has partitioned pores.

In the present invention, the porous fiber has innumerable fine pores continuously in its outside and inside. Such a pore structure serves as a flow path to efficiently lead the substance to be removed in the fluid that is to be treated to the granular material in the fiber. Further, when the substance to be removed is a high molecular weight compound, such a pore structure fixes and adsorbs the high molecular weight compound within the pore, thereby the high molecular weight compound can be removed.

Thus, in the present invention, the three-dimensional pore structure preferably has the average radius of pores in a specific range. That is, in the porous fiber of the present invention, the three-dimensional pore structure preferably has the average radius of pores in the range of 0.5 nm or more and 100 nm or less. The lower limit of the average radius of pores of the three-dimensional pore structure is preferably 0.5 nm, more preferably 1.5 nm, and particularly preferably 2.0 nm, and the upper limit is preferably 100 nm, more preferably 40 nm, and particularly preferably 25 nm. When the average radius of pores is small, the substance to be removed does not enter the pore, and thus adsorption efficiency may decrease. Meanwhile, when the pore radius is too large, the substance to be removed may fall off without being fixed on voids, and the adsorption efficiency may decrease. Within the above-mentioned pore size range, an optimum pore size exists corresponding to the size of the substance to be removed. When the average radius of pores is in the above-mentioned range, the low molecular weight compound is efficiently led to the granular material in the fiber and easily adsorbed and removed, and at the same time, the high molecular weight compound remains inside the pore of the porous fiber and is easily adsorbed and removed.

In the porous fiber of the present invention, it is preferable that the pore in the three-dimensional pore structure selectively adsorb a high molecular weight compound having a molecular weight of 1000 or more. The molecular weight of the high molecular weight compound to be selectively adsorbed is more preferably 2,000 or more, further preferably 3,000 or more, and still preferably 5,000 or more. A compound having a high molecular weight can be selectively adsorbed with enlarged pores; however, the strength of the porous fiber is insufficient when the pore is too large. Thus, the upper limit is preferably 1,000,000, more preferably 800,000, further preferably 500,000, and still preferably 200,000. "Selectively adsorbing a high molecular weight compound having a molecular weight of 1000 or more" herein means that the pore adsorbs the high molecular weight compound having a molecular weight of 1000 or more more than the low molecular weight compound having a molecular weight of less than 1000 within the blood concentration range of a dialysis patient. The method of determining whether the pore selectively adsorbs a high molecular weight compound having a molecular weight of 1000 or more is as follows: a section of the porous fiber having a thickness of 1 μm in a direction of the fiber length is produced with a microtome, and a sample not containing a granular material and a sample containing a granular material are produced. The sample not containing a granular material (50 mg) and a sample containing a granular material (50 mg) are immersed in 50 mL of bovine plasma, permeated with the plasma at 37° C. for 4 hours, and then the adsorption capability per 1 g (adsorption mass per 1 g) is determined from the difference between the concentrations before and after the immersion. When the sample not containing a granular material adsorbs a high molecular weight compound having a molecular weight of 1000 or more more than the sample containing a granular material, the sample not containing a granular material is determined to selectively adsorb a high molecular weight compound having a molecular weight of 1000 or more. The method of determining the adsorption mass per 1 g differs depending on the substance to be adsorbed. For example, when the low molecular weight compound having a molecular weight of 1000 or less is urea, uric acid, or creatinine, the adsorption mass per 1 g can be determined by an enzymatic method. In the case of inorganic phosphorus, the adsorption mass per 1 g can be determined by the molybdic acid direct method. Meanwhile, when the compound having a molecular weight of 1 kDa or more is β2-MG, the adsorption amount can be determined by the latex immunoagglutination method. In the specification, the molecular weight of 1000 may be described simply as 1 kD. To selectively adsorb a high molecular weight compound having a molecular weight of 1 kDa or more, the porous fiber preferably has an average radius of pores within the above-mentioned range.

The high molecular weight compound as the substance to be removed is not particularly limited.

The porous fiber of the present invention is preferably used for medical use. "The porous fiber of the present invention is used for medical use" means that the porous fiber of the present invention is used, for example, in the following medical devices. That is, examples of the medical devices include, without particular limitation, a dialysis membrane used in dialysis and an adsorption column used to adsorb toxic substances in blood with being in direct contact with blood. When the porous fiber of the present invention is used for medical use, examples of the toxic substances include, among substances present in blood, a substance that is harmful in nature and a substance that has a harmful effect when the substance is present in excessive amount. Examples of the high molecular weight compound that is harmful or has a harmful effect include a cytokine, HMGB1, tumor-producing protein, $\beta_2$ microglobulin (($\beta$2 MG), α1 microglobulin (α1MG), anti-A antibody, anti-B antibody, anti-acetylcholine receptor antibody, and anti-cardiolipin antibody, anti-DNA antibody, an immune complex, bile acid, a coma substance, an agent, and a rheumatoid factor. Meanwhile, an albumin (molecular weight: 66 kDa), a nutritional protein, is preferably adsorbed at minimum. That is, examples of the substance to be removed include a cytokine (molecular weight: 8 to 30 kDa), β2MG (molecular weight: 12 kDa), HMGB1 (molecular weight: 30 kDa), and α1MG (molecular weight: 33 kDa). In particular, examples of the substance to be removed include 2MG, which is said to be insufficiently removed in extracorporeal circulation.

In the present invention, a cytokine refers to a protein that acts on cell proliferation, differentiation, and functional expression. Examples of the cytokine include interleukin-1β, interleukin-2, interleukin-3, interleukin-4, interleukin-6, interleukin-8, TNFα, M-CSF, G-CSF, GM-CSF, interferon α, interferon β, interferon γ, TGF-β, SCF, EMP, EGF, KGF, FGF, IGF, PDGF, HGF, and VEGF. The cytokine in the present invention is an inflammatory cytokine, and particular examples of the cytokine include interleukin-1β, interleukin-6, interleukin-8, and TNFα.

When the average radius of pores of the three-dimensional pore structure is within the above-mentioned range, these substances to be removed can be efficiently adsorbed to the porous fiber of the present invention.

The average radius of pores of the porous fiber of the present invention can be determined by differential scanning calorimetry (DSC) using a differential scanning calorimeter (DSC). Specifically, it is determined as a primary average radius of pores by measuring the degree of freezing point depression due to capillary aggregation of water within pores. The measurement is performed while rapidly cooling the adsorption material to −55° C. and heating it to 5° C. at 0.3° C./min. The peak top temperature of the obtained curve is taken as the melting point, and the primary average radius of pores is calculated from the Formula 1 below. For the measurement/calculation method, see the description in p. 104 of the literature (Kazuhiko Ishikiriyama et al.; JOURNAL OF COLLOID AND INTERFACE SCIENCE, VOL. 171, 103-111(1995)).

Primary average radius of pores [nm]×(33.30−
0.3181×melting point depression [° C.])/melting
point depression [° C.]                    Formula 1

The adsorption capability of the porous fiber of the present invention can be further improved by increasing the specific surface area of pores to adsorb the substance to be removed. Thus, in the porous fiber of the present invention, the three-dimensional pore structure preferably has the specific surface area of pores of 10 m$^2$/g or more. The lower limit of the specific surface area of pores is preferably 10 m$^2$/g, more preferably 20 m$^2$/g, further preferably 30 m$^2$/g, still preferably 40 m$^2$/g, and particularly preferably 50 m$^2$/g. Meanwhile, when the specific surface area of pores is too large, the mechanical strength of the porous fiber is insufficient. Thus, the upper limit of the specific surface area of pores is preferably 1000 m$^2$/g, more preferably 800 m$^2$/g, further preferably 650 m$^2$/g, and still preferably 500 m$^2$/g.

The measurement of the specific surface area of pores is performed using DSC in the same manner as in the measuring method of the average radius of pores. The calculation method of the specific surface area of pores is as described in p. 104 of the above-mentioned document.

The porous fiber of the present invention has a granular material having a particle diameter of 200 μm or less. The particle diameter of the granular material is preferably as small as possible, and thus, the diameter is preferably 200 μm or less, more preferably 100 μm or less, and particularly preferably 50 μm or less. The particle diameter is preferably 200 μm or less, because, when the diameter is 200 μm or less, for example, in the case where the granular material is supported inside the porous fiber, the spinneret is less likely to be clogged during spinning and the spinning capability is less likely to be reduced. The smaller the particle diameter, the larger the specific surface area, and thus, the adsorption efficiency tends to be increased. However, when the particle diameter is smaller than that of the pore of the porous fiber, the granular material may pass through the pore and be eluted into the fluid that is to be treated such as blood. Thus, the diameter is preferably larger than the pore size, and specifically the particle diameter is preferably more than 100 nm. However, when the granular material is an aggregate of primary particles, the particle diameter of the aggregate of primary particles needs to be within the above-mentioned range of the diameter, and the particle diameter of primary particles does not need to be within the above-mentioned range of the diameter.

The particle diameter of the granular material supported by the porous fiber is observed with a scanning electron microscope (for example, S-5500 manufactured by Hitachi High-Technologies Corporation). First, the porous fiber is sufficiently moistened, and then immersed in liquid nitrogen to instantaneously freeze water in the pore with liquid nitrogen. Then, the porous fiber is immediately folded, and the frozen water is removed in a vacuum dryer at 0.1 torr or less with the section of the porous fiber being exposed, thereby a dried sample is obtained. Then, a thin film of platinum (Pt), platinum-palladium (Pt—Pd) or the like is formed on the surface of the porous fiber by sputtering to obtain an observation sample. The section of the sample is observed with a scanning electron microscope. An electron microscope image of the section of the fiber in the field including the granular material is taken with a scanning electron microscope (1000×), the diameters of 30 randomly selected particles of the granular material are measured, and the number average is taken as the diameter. When the shape is other than a circle, $(a \times b)^{0.5}$ is determined as the diameter of an equivalent circle, where a is the diameter of the circle inscribed in the shape, and b is the diameter of the circle circumscribed in the shape. When the granular material is an aggregate, the diameter of the circle inscribed in the aggregate is determined as the diameter of an equivalent circle in the same manner as described above, where a is the diameter of the circle inscribed in the aggregate, and b is the diameter of the circle circumscribed in the aggregate.

The inscribed circle is a circle that is inscribed at least at two points in a curve forming the contour of the fiber cross section, is only inside the fiber, and has the largest possible diameter in the range in which the circumference of the inscribed circle and the curve forming the contour of the fiber do not intersect. The circumscribed circle is a circle that has the maximum diameter among the circles that pass through any two points in the contour of the fiber cross section.

It is important to reduce the risk of the granular material peeling off from the broken section of the fiber and flowing out when the porous fiber is broken by the external physical force. Thus, the granular material used in the present invention is preferably used with being supported inside the porous fiber. The state in which the granular material is supported inside mainly refers to a state in which the granular material is physically mixed with the porous fiber without impairing the function of the granular material, and is attached to the inside of the porous fiber and kept. However, the state in which the granular material is supported inside is not necessarily limited to a state in which the granular material is physically mixed with the porous fiber, but includes a state in which the granular material is chemically bonded to the constituent molecule inside the porous fiber as long as the function of the granular material is not impaired.

In the present invention, the granular material supported inside the porous fiber has an area occupancy rate, in a cross section of the three-dimensional pore structure, of 3.0% or more. The lower limit of the area occupancy rate is preferably 5.0%, more preferably 10%, and further preferably 20%. The upper limit of the area occupancy rate is preferably 80%, more preferably 70% or less, and further preferably 60% or less. When the area occupancy rate of the granular material is 3.0% or more, in a column including the porous fiber, the amount of the porous fiber necessary for exhibiting sufficient adsorption capability can be easily reduced, and the column volume can be easily reduced. Meanwhile, the granular material preferably has an area occupancy rate in a cross section of the porous fiber of 80% or less, because, in such a case, sufficient fiber strength of the porous fiber is easily obtained and the spinnability tends to be good. Because the granular material is supported by the fiber material, peeling off from the yarn section of the granular material is easily suppressed in the case where the fiber is broken by the external pressure.

The area occupancy rate of the granular material in the cross section of the porous fiber can be measured by the following method.

First, the porous fiber is sufficiently moistened, and then immersed in liquid nitrogen to instantaneously freeze water in the pore with liquid nitrogen. Then, the porous fiber is immediately folded, and the frozen water is removed in a vacuum dryer at 0.1 torr or less with the section of the porous fiber being exposed, thereby a dried sample is obtained. Then, a thin film of platinum (Pt), platinum-palladium (Pt—Pd) or the like is formed on the surface of the porous fiber by sputtering to obtain an observation sample. The section of the sample is observed with a scanning electron microscope (for example, S-5500 manufactured by Hitachi High-Technologies Corporation). A transparent sheet is overlaid on a printed image of an electron microscope image of a randomly selected section of the fiber with a scanning electron microscope (400×), and the granular material is filled in black with a black pen or the like. The scale bar is also accurately traced with a ruler and a black pen. Then, the transparent sheet is copied to white paper, and thus the granular material, black, is clearly distinguished from the part other than the granular material, white. Then, the area occupancy rate (%) of the granular material can be determined using image analysis software. As the image analysis software, for example, "Analyze Particles" of "Image J" (developed by Wayne Rasband (NIH)) can be used for measurement and to determine the total area of the granular material. The area rate occupied by the granular material, that is, the area occupancy rate (%) is determined by the following Formula 2. For the electron microscope image of the section of the porous fiber, images of 30 randomly selected sections of the porous fiber are taken, and the average is used for the calculation.

Area occupancy rate of granular material (%)=total area of granular material/cross section of fiber× 100%     Formula 2

It is important that the porous fiber of the present invention does not have the granular material having a particle diameter of 200 µm or less in a region within 1.0 µm in a depth direction from an outermost surface.

"In a depth direction from an outermost surface" means that the direction is in the depth direction, that is, toward the center of the porous fiber at the angle perpendicular to the surface of the porous fiber. "A region within 1.0 µm" refers to the whole region including the region at depth 1.0 µm and the region in the outer surface side from that. Thus, it means that "the porous fiber does not have the granular material" in the outer surface side of the above-mentioned part.

By reducing the amount of the granular material exposed on the outermost surface of the porous fiber, the exposure of the granular material to the fluid that is to be treated can be easily suppressed, and the damage on the granular material caused by the flow stress can be easily prevented. Such a structure is particularly preferable in the case where blood is used as the fluid that is to be treated, because the direct contact between the granular material and hemocytes is suppressed and activation of blood can be easily reduced.

"Does not have the granular material" in the present invention is defined as follows. That is, the amount contained in the region within 1.0 µm in a depth direction from an outermost surface in the cross section of the porous fiber is 3% or less in the total amount of the granular material contained in the cross section of the porous fiber. The amount is more preferably 2% or less, further preferably 1% or less, and still preferably 0.5% or less.

When the section of the fiber is other than a circle, 12 radiuses passing through the center point of the circumscribed circle of the fiber cross section are selected at 30 degree intervals, the points at 1 µm from the outer surface in the radiuses are connected, and the connected line is used as the line to indicate the region within 1 µm from the outer surface. The rate of the granular material contained in the region within 1.0 µm in the depth direction from the outermost surface in the cross section of the porous fiber can be measured by the following method.

First, an observation sample is prepared in the same manner as in the measurement of the area occupancy rate, and the section of the sample is observed with a scanning electron microscope (for example, S-5500 manufactured by Hitachi High-Technologies Corporation). A transparent sheet is overlaid on a printed image of an electron microscope image of a randomly selected section of the fiber with a scanning electron microscope (400×), and the granular material is filled in black with a black pen or the like. Then, the transparent sheet is copied to white paper, thus the granular material, black, is clearly distinguished from the part other than the granular material, white, the area of the granular material contained in the entire section of the fiber (A1) and the area of the granular material contained within 1 µm (A2) are determined with image analysis software, and the rate of the granular material contained in the region within 1 µm is determined from A2/A1×100%. For the electron microscope image of the section of the porous fiber, images of 30 randomly selected sections of the porous fiber are taken, and the average is used for the calculation.

Examples of the method of producing a porous fiber that does not have the granular material having a particle diameter of 200 µm or less in a region within 1.0 µm in a depth direction from an outermost surface include a method in which a core liquid containing the granular material and a sheath liquid containing no granular material are used in spinning of a porous fiber having a core-sheath structure described below.

In the present invention, examples of the granular material that can be supported inside a fiber include carbon granular materials such as charcoal, bamboo charcoal, active carbon, carbon fiber, molecular sieve carbon, carbon nanotube, graphene, graphite, graphene oxide, and mesoporous carbon, inorganic particles such as silica gel, macroporous silica, active alumina, zeolite, smectite, hydroxyapatite, metal hydroxide, metal hydrous oxide, and metal carbonate, and organic particles such as ion exchange resin, chelate resin, organic metal complex, chitosan, and cellulose, and inorganic mesoporous material, organic-inorganic hybrid mesoporous material, and carbon gel, and one or more of these can be used.

In the present invention, it is preferable that the granular material selectively adsorb a low molecular weight compound having a molecular weight of less than 1000. "Selectively adsorbing a low molecular weight compound having a molecular weight of less than 1000" herein means that the granular material adsorbs the low molecular weight compound having a molecular weight of less than 1000 more than the high molecular weight compound having a molecular weight of 1000 or more within the blood concentration range of a dialysis patient. The method for determining whether the granular material selectively adsorbs a low molecular weight compound having a molecular weight of less than 1000 is as follows: samples are prepared in the same manner as in the above-mentioned method of determining whether the pore selectively adsorbs a high molecular weight compound having a molecular weight of 1000 or more, immersed in bovine plasma, and when the sample containing a granular material has higher adsorption capability per 1 g than that of the sample not containing a granular material, the granular material is determined to selectively adsorb a low molecular weight compound having a molecular weight of less than 1 kDa. The method of determining the adsorption capability per 1 g is also the same as in the above-described method of determining whether the pore selectively adsorbs a high molecular weight compound having a molecular weight of 1000 or more.

The low molecular weight compound having a molecular weight of less than 1 kDa is not particularly limited, and examples thereof include phosphoric acid, urea, uric acid, creatinine, indoxyl sulfate, and homocysteine. Such low molecular weight compounds are substances to be removed in extracorporeal circulation, because they are waste products deposited in the body of a dialysis patient.

In one example, when an ionic low molecular weight compound such as phosphoric acid is a substance to be removed, the granular material in the porous fiber of the present invention is preferably inorganic particles. In the porous fiber of the present invention, it is preferable that the granular material be inorganic particles and have phosphorus adsorption capability. Examples of the preferred inorganic particles include a titanium oxide complex, a rare earth element hydroxide, a rare earth element hydrous oxide, and a rare earth element carbonate. The rare earth element refers to 17 elements in total of two elements of scandium (Sc) of atomic number 21 and yttrium (Y) of atomic number 39, and 15 elements from lanthanum (La) of atomic number 57 to lutetium of atomic number 71, La, Ce, Pr, Nd, Pm, Sm, Eu, Gd, Tb, Dy, Ho, Er, Tm, Yb, and Lu, in the position of the periodic table. Among them, carbonates of rare earth elements have low solubility in water and, further, have small pH change in physiological saline, and thus, they can be particularly preferably used for medical use.

Further, in the inorganic particles, the rare earth element is most preferably selected from the group consisting of lanthanum, cerium, praseodymium, samarium, and neodymium. In this case, carbonates of rare earth elements are lanthanum carbonate, cerium carbonate, praseodymium carbonate, samarium carbonate, and neodymium carbonate. These carbonates of rare earth elements are particularly suitable for extracorporeal circulation because they have low solubility in water, small pH change, and further, high adsorption capability of ionic low molecular weight compounds.

The extracorporeal circulation in the present invention means that blood in an organism is led outside the body, for example, to remove a predetermined substance, and then is returned to the body again.

As another example, when uremic toxin, a low molecular weight compound, is a substance to be removed, the granular material in the porous fiber of the present invention preferably includes at least one selected from the group consisting of active carbon, carbon nanotube, graphene, graphite, and graphene oxide. The specific surface area of the granular material is preferably 100 to 2500 $m^2/g$, more preferably 200 to 2000 $m^2/g$, and most preferably 300 to 1500 $m^2/g$. When the specific surface area is in the above-mentioned range, the adsorption and removal capability of these carbon granular materials can be exhibited well. Examples of the uremic toxin include urea, uric acid, creatinine, indoxyl sulfate, and homocysteine.

The granular material according to the present invention preferably has high insolubility in water. That is, the granular material preferably has low solubility in water. The insolubility in water means that the solubility in 100 g of water is 1 mg or less, and the above-mentioned solubility is more preferably 0.1 mg or less, and the solubility is most preferably 0.01 mg or less.

In the measurement of the above-mentioned solubility, 100 g of water kept at 20° C. in a thermostat and a rotor are put into a flask, 1 mg of granular material to be measured is put there, and the mixture is stirred for 12 hours or more. Then, the resulting product is filtered with No. 5A filter paper, the residue is dried at 60° C. with the filter paper to a constant weight, and the insoluble component is weighed. The difference between the input amount of 1 mg and the weight of the insoluble component is taken as the solubility in 100 g of water. When the insoluble component is not filtered out, the solubility is more than 1 mg.

The porous fiber of the present invention preferably has a pH change of −1 or more and +1 or less.

The porous fiber of the present invention more preferably has a pH change of −1.0 or more and +1.0 or less. The porous fiber of the present invention further preferably has a pH change of −0.8 or more and 0.8 or less (within ±0.8), still preferably has a pH change of within ±0.6, and particularly preferably has almost no pH change, that is, has a pH change of within ±0.1.

In general, pH balance in the environment and in an organism is very important, and in particular, imbalance in an organism leads to various diseases. The porous fiber of the present invention causes a small pH change of physiological blood when the porous fiber of the present invention is in contact with blood, and thus has little influence on the pH of body fluid such as blood. In the present invention, the pH change in physiological saline is used as an indicator of whether the porous fiber of the present invention has excellent pH balance in an organism. Specifically, the pH change between the pHs before and after the porous fiber is put in physiological saline and stirred at 200 rpm for 4 hours is measured.

As a pH measuring method, a glass electrode method, which is a measuring method most generally used, is used. This is a method in which two electrodes of a glass electrode and a reference electrode are used, and the voltage (potential difference) generated between the two electrodes is measured to determine the pH of a target solution. Specifically, a compact pH meter, LAQUAtwin manufactured by HORIBA, Ltd. and the like can be used. In this instrument, the pH scale is first calibrated using known standard buffers (pH 4.01 and 6.86). The pH of physiological saline is measured and used as the pH (start). Then, 0.1 g of the fiber to be measured is weighed, 10 mL of the same physiological saline as above is added thereto, and the mixture is stirred at room temperature for 4 hours. One mL is sampled and centrifuged at 9000 rpm for 5 minutes, 500 μL of the supernatant is added to the measuring chamber, and pH is measured and taken as pH (4H). The pH change can be determined by the Formula 3.

$$\text{pH change} = \text{pH (4H)} - \text{pH (start)} \qquad \text{Formula 3}$$

The porous fiber of the present invention preferably has a surface porosity of 0.5% or more and 30.0% or less. The porous fiber of the present invention preferably has a surface porosity of 0.5% or more, more preferably has a surface porosity of 1.5% or more, and particularly preferably has a surface porosity of 2.0% or more. The porosity is preferably high, because, when the porosity is high, the substance to be removed in the fluid that is to be treated tends to diffuse to the adsorption site inside the fiber. Meanwhile, the upper limit of the porosity is preferably 30%, more preferably 16%, and further preferably 12%. The porosity is preferably 30% or less, because, when the porosity is 30% or less, the fiber strength can be improved, and the increase in surface roughness can be suppressed. In addition, flowing out of fine particles produced inside the pore to the outside of the fiber can be easily suppressed.

The measuring method of the surface porosity is as follows: the section of the fiber obtained by the same method as in the observation sample produced when the area occupancy rate of the granular material is measured is observed with a scanning electron microscope (S-5500, manufactured by Hitachi High-Technologies Corporation) at 50,000×, and the image is saved in a computer. The size of the image saved is preferably 640 pixels×480 pixels. The SEM image (6 μm×6 μm) is cut out at a randomly selected position, and is subjected to image analysis with image processing software. A threshold is determined so that the structure part has high brightness and the other parts have low brightness by a binarizing process, and an image in which the high brightness part is white and the low brightness part is black is obtained. When the structure part and the other parts cannot be divided because of the small difference in contrast in the image, the image is cut at the part having similar contrast ranges, the cut images are each binarized, and then connected back to one image. Alternatively, the part other than the structure part can be filled in black to perform image analysis. The image contains noise, and the noise cannot be distinguished from pores in the low brightness part having continuous pixels of 5 or less. Thus, the low brightness part is taken as the high brightness part as a structure part. As a method of eliminating noise, the low brightness part having continuous pixels of 5 or less is removed on the measurement of the number of pixels. Alternatively, the noise part can be filled in white. The number of pixels in the low brightness part is measured, and the percentage of the number of pixels in the low brightness part in the total number of pixels in the analysis image is calculated and taken as the porosity. The same measurement is performed on 30 images, and the average value is calculated.

The form of the porous fiber in the present invention is a solid yarn. In the case of a solid yarn, the shape of the yarn section is not limited to a true circle, and the section can have a deformed shape. Examples of the deformed shape of the section include an oval, a triangle, and a multifoil. When the section has a deformed shape, the surface area per solid yarn volume can be increased, and the adsorption capability can be improved.

The porous fiber of the present invention preferably has a low risk in terms of mechanical safety of the fiber, spinnability, and the peeling off of the granular material. Thus, the porous fiber of the present invention preferably has a core-sheath structure or a sea-island structure. Also, such a low risk can be achieved by a method in which the outer surface of the polymer internally containing the granular material is further coated with the same or a different polymer, as long as the number of the pore can be increased and the pore can be controlled without peeling off of the granular material internally contained.

In the case of the porous fiber having a core-sheath structure, though the structure can be of a concentric type or eccentric type, the concentric type is preferably employed from the viewpoint of the stability of the porous fiber and the prevention of the exposure of granular material.

The porous fiber having a core-sheath structure preferably has a thickness of the sheath of 0.1 μm or more and 50 μm or less. When the sheath is too thin, the spinnability is poor, and the granular material may be eluted. Meanwhile, when the sheath is too thick, the substance to be removed contained in the fluid that is to be treated cannot diffuse into the inside of the fiber, and the adsorption capability of the granular material may not be sufficiently exhibited.

In the porous fiber having a core-sheath structure, the materials of the core and the sheath can have the same composition or different compositions, but it is preferable that they have similar viscosities. The difference in viscosity is preferably small, because, when the difference in viscosity is small, peeling is less likely to occur at the core-sheath interface.

In the present invention, the sea-island structure refers to a multicore sea-island structure having a plurality of island components, and the granular material is preferably contained in the island component from the viewpoint of reducing the exposure of the granular material. By increasing the number of islands, the adsorption efficiency of the granular material internally contained in the island component can be increased. The number of islands in the sea-island structure is preferably 2 or more and 300 or less. In particular, considering the spinneret design, spinning operability, fiber physical properties, processability and capability of the adsorbent, the number of islands are more preferably 5 to 50.

The porous fiber of the present invention is not limited to a porous fiber having a core-sheath structure or a porous fiber having a sea-island structure only, and can be a porous fiber of a usual monofilament, a bimetal fiber, multilayer structure type fiber or the like.

In the porous fiber of the present invention, the fiber having a solid shape preferably has a yarn diameter in a range of 20 μm or more and 1000 μm or less. The lower limit of the yarn diameter of the fiber having a solid shape is preferably 20 μm, more preferably 50 μm, and further preferably 100 μm. The upper limit is preferably 1000 μm, more preferably 800 μm, and further preferably 500 μm. When the yarn diameter of the fiber having a solid shape is 20 μm or more, the fiber strength is unlikely to be reduced even when the particle addition rate is increased, and thus the productivity tends to be improved. Meanwhile, when the yarn diameter of the fiber is 1000 μm or less, the packing rate of the porous fiber packed in the adsorption column tends to be high, and the adsorption capability tends to be improved.

The measuring method of the yarn diameter of the fiber is as follows: 50 yarns (fibers) are randomly extracted from the yarns packed in the adsorption column. After washing the extracted yarns (fibers), the washing solution is completely replaced with pure water, and the yarns are sandwiched between a slide glass and a cover glass. The outer diameter (the diameter of the outermost periphery) of the yarn is measured at any two points per yarn using a projector (for example, V-10A manufactured by Nikon Corporation), and the average is calculated and rounded off to the nearest integer. When the number of packed yarns is less than 50, all the yarns are measured and the average is determined in the same way.

Though the material of the porous fiber in the present invention is not particularly limited, an organic material is suitably used from the viewpoint of easy molding, cost, and the like. Examples of the material used include polymethyl methacrylate (hereinafter referred to as PMMA), polyacrylonitrile (hereinafter referred to as PAN), polysulfone, polyethersulfone, polyarylethersulfone, polypropylene, polystyrene, polycarbonate, cellulose, cellulose triacetate, and ethylene-vinyl alcohol copolymer. Among them, the porous fiber preferably include a material that is an amorphous high molecular weight compound and has properties capable of adsorbing proteins, and examples of the material include PMMA and PAN. PMMA and PAN are preferable because a structure having a sharp pore size distribution tends to be obtained. The porous fiber of the present invention particularly preferably includes polymethyl methacrylate (PMMA). PMMA is excellent in moldability and cost, and has high transparency, and thus, the internal state of the porous fiber can be relatively easily observed, and the fouling state can be easily evaluated. However, the porous fiber can include a small amount of other components.

The porous fiber can have a negative charge. By including a functional group having a negative charge in at least a part of the material, the porous fiber has increased hydrophilicity, and tends to be finely dispersed (that is, a large number of pores are formed).

Examples of the material include a material having a substituent such as a sulfo group, a carboxyl group, an ester group, a sulfite group, a hyposulfite group, a sulfide group, a phenol group, and a hydroxy silyl group as a functional group having a negative charge. Among them, the functional group is preferable at least one selected from a sulfo group, a carboxyl group, and an ester group.

Examples of those having a sulfo group include vinyl sulfonic acid, acrylic sulfonic acid, methacrylic sulfonic acid parastyrene sulfonic acid, 3-methacryloxypropane sulfonic acid, 3-acryloxypropane sulfonic acid, 2-acrylamido-2-methylpropane sulfonic acid, and sodium salts, potassium salts, ammonium salts, pyridine salts, quinoline salts, and tetramethyl ammonium salts thereof.

The amount of the negative charge is preferably 5 µeq or more and 30 µeq or less per 1 g of a dried fiber.

The amount of the negative charge can be measured, for example, using a titration method.

Though, as the production example of the adsorption column according to the present invention, an example in which, for a yarn form, a porous fiber having a core-sheath structure is used is shown below, the present invention is not limited to this.

In particular, as an example, in the field of blood purification for medical use, it is known that various dialysis complications such as hyperphosphatemia caused by insufficient removal of inorganic phosphorus and dialysis-related amyloidosis caused by insufficient removal of β2MG occur. Currently, for the treatment of hyperphosphatemia, an oral phosphate adsorbent is used, and for dialysis-related amyloidosis, a β2MG removal column in which porous cellulose beads are incorporated is used. However, if it is possible to simultaneously adsorb and remove inorganic phosphorus and β2MG, QOL of patients will be improved.

Thus, for the evaluation of the adsorption capability of the porous fiber in the present invention, inorganic phosphorus was evaluated as the substance to be removed of a low molecular weight compound of less than 1 kDa, and β2MG was evaluated as a substance to be removed of a high molecular weight compound of 1 kDa or more.

When the adsorption fiber has low adsorption capability per surface area, the fiber is not preferable as an adsorption material, and does not exhibit good adsorption capability when the fiber is packed in an adsorption column or the like. To obtain sufficient adsorption capability, the increased number of fibers has to be packed, which leads to an increase in the column volume, resulting in an increase in cost and a decrease in handleability. In particular, when the fluid that is to be treated is blood, the amount of blood taken out from the body increases, which may cause a serious side effect such as a decrease in blood pressure. Thus, when the substance to be removed is inorganic phosphorus, the adsorption capability of the fiber is preferably 1.0 mg/cm$^3$ or more, more preferably 2.0 mg/cm$^3$ or more, further preferably 3.0 mg/cm$^3$ or more, and particularly preferably 4.0 mg/cm$^3$ or more. In the present invention, the granular material having phosphorus adsorption capability means that the fiber has the adsorption capability of inorganic phosphorus of 1.0 mg/cm$^3$ or more.

Meanwhile, when the substance to be removed is β2MG, the adsorption capability of the fiber is preferably 0.010 mg/cm$^2$ or more, more preferably 0.015 mg/cm$^2$ or more, further preferably 0.020 mg/cm$^2$ or more, and particularly preferably 0.030 mg/cm$^2$ or more.

[Production of Porous Fiber]

A polymer of the raw material of the core is dissolved in a suitable solvent, then a predetermined amount of a selected granular material is added thereto to prepare a core liquid. The solvent varies depending on the type of the polymer, and generally used are dimethylformamide, dimethyl sulfoxide, hexanone, xylene, tetralin, cyclohexanone, carbon tetrachloride and the like. For example, when PMMA is used as the polymer, dimethyl sulfoxide (DMSO) is preferably employed.

The viscosity of the spinning solution is important for the production of the porous fiber. That is, when the viscosity is too low, the fluidity of the spinning solution is high, and maintaining a desired shape is difficult. Thus, the lower limit of the viscosity of the spinning solution is 10 poise, more preferably 90 poise, further preferably 400 poise, and particularly preferably 600 poise. Meanwhile, when the viscosity is too high, the stability of discharge may decrease due to an increase in pressure loss at discharge of spinning solution, and mixing of the spinning solution may be difficult. Thus, the upper limit of the viscosity of the spinning solution at a temperature in the spinneret is 100,000 poise, and more preferably 50,000 poise.

The spinning solution for a polymer serving as a raw material of sheath liquid and the spinning solution for core liquid preferably have close viscosities, more preferably have the same composition.

The spinning method for obtaining the fiber in the present invention can be melt spinning or solution spinning. However, the solution spinning is preferable, because, in the solution spinning, a support component can be uniformly dissolved in a solvent and then only the solvent can be rapidly removed therefrom, and thus a porous fiber having a relatively uniform structure tends to be obtained. Thus, the spinning solution is preferably composed of a matrix component such as a polymer and a solvent in which the matrix component can be dissolved.

Hereinafter, the spinning method will be described with an example of a porous fiber having a core-sheath structure in solution spinning. The spinning solution is discharged from a spinneret, and coagulated into a shape of a solid yarn in a coagulating bath. Examples of the spinneret for obtaining a porous fiber having a core-sheath structure include a double tube shape and a triple tube shape with an annular slit, and in particular, the double tube shape is preferable. In the double tube shape, the core liquid is discharged from the inner tube, and the sheath liquid is discharged from the outer tube. Though the discharge rates of the core liquid and the sheath liquid can be controlled with one gear pump, it is more preferable to connect a gear pump to each of the liquids and control them. By controlling them with two gear pumps, the discharge rates of the core and the sheath can be easily changed. For example, if the discharge rate of the sheath is reduced while the discharge rate of the core is kept constant, a fiber with a thin sheath can be obtained.

In the case of a porous fiber having a sea-island structure, though a usual spinneret for a sea-island fiber can be used, the spinneret preferably has a design in which island parts are evenly distributed. The coagulating bath is usually composed of a coagulant such as water or alcohol, or a mixture of a solvent that constitutes the spinning solution and a coagulant. Void percentage of the fiber can be changed by controlling the temperature of the coagulating bath. The void percentage can be affected by the type and the like of the spinning solution, and thus the temperature of the coagulating bath is appropriately selected. In general, the void percentage can be increased by increasing the temperature of the coagulating bath. Though the mechanism has not been exactly revealed, it is thought that, in the competitive reaction between the desolvation from the spinning solution and the coagulation shrinkage, the desolvation is fast in a bath at a high temperature, and the fiber is coagulated and fixed before it shrinks. However, when the temperature of the coagulating bath is too high, the pore size becomes too large. Thus, for example, the temperature of the coagulating bath is preferably 20° C. or more when the fiber to be obtained is a solid yarn including PMMA as a material and gas is introduced into the inner tube.

Next, a step of washing off the solvent attached to the coagulated solid yarn is performed. Though the method for washing the solid yarn is not particularly limited, a method in which the solid yarn passes through a bath having multistage water (referred to as a water washing bath) is preferably used. The temperature of water in the water washing bath can be determined according to the nature of the polymer that constitutes the yarn. For example, in the case of a yarn including PMMA, the temperature is 30 to 50° C.

In order to maintain the pore size of the solid yarn after passing through the water washing bath, a step of applying a moisturizing component can be performed. The moisturizing component as used herein refers to a component capable of maintaining the humidity of the solid yarn or a component capable of preventing the decrease in humidity of solid yarn in the air. Typical examples of the moisturizing component include glycerin and aqueous solutions thereof.

After water washing and applying a moisturizing component, in order to increase the dimensional stability of the solid yarn with high shrinkage, a step of a bath filled with an aqueous solution of a heated moisturizing component (referred to as a heat treatment bath) can be performed. The heat treatment bath is filled with a heated aqueous solution of a moisturizing component. When the solid yarn passes through the heat treatment bath, the solid yarn shrinks due to thermal action and tends not to shrink in the subsequent steps, resulting in a stable yarn structure. Though the heat treatment temperature at this time varies depending on the material of the yarn, in the case of the yarn including PMMA, the temperature is preferably 75° C. or more, and more preferably 82° C. or more. The temperature is preferably 90° C. or less, and more preferably 86° C. or less. The fiber thus spun is wound up around a spool and converged.

[Production of Adsorption Column]

The adsorption column of the present invention is an adsorption column including the porous fiber of the present invention packed into the adsorption column.

One example of the method to produce the adsorption column of the present invention using the porous fiber having a core-sheath structure produced as above is shown below.

For the casing shape of the adsorption column, both ends of the adsorption column are open ends, and examples of the casing shape include a rectangular cylinder such as a square cylinder and a hexagonal cylinder, and a round cylinder. Among them, a round cylinder, in particular, a cylinder whose cross section is a true circle, is preferable. This is because the casing has no corner, and the retention at the corner of blood, the fluid that is to be treated, can be suppressed. Further, when the both ends are open ends, the flow of the fluid that is to be treated is unlikely to become turbulence, and pressure loss can be easily minimized.

The casing is preferably an apparatus that is composed of a plastic, a metal or the like. In the former case, the casing is produced by injection molding with a mold or cutting of a material. In the latter case, the apparatus is produced by cutting a material. Among them, the plastic is preferably used from the view point of cost, moldability, weight, and blood compatibility.

In the case of a plastic, for example, a thermoplastic resin that is excellent in mechanical strength and thermostability is used. Specific examples of such a thermoplastic resins include a polycarbonate resin, a polyvinyl alcohol resin, a cellulose resin, a polyester resin, a polyarylate resin, a polyimide resin, a cyclic polyolefin resin, a polysulfone resin, a polyethersulfone resin, a polyolefin resin, a polystyrene resin, a polyvinyl alcohol resin, and mixtures thereof. Among these, polystyrene, polycarbonate, and derivatives thereof are preferred from the viewpoint of moldability, transparency, and radiation resistance, which are required for the casing. This is because a resin excellent in transparency allows the inside during hemoperfusion to be checked and thus is suitable for securing safety, and a resin excellent in radiation resistance is preferable in the case where radiation is performed during sterilization.

The casing length of the adsorption column of the present invention is preferably 1 cm or more and 500 cm or less, and more preferably 3 cm or more and 50 cm or less. The casing length is the axial length of the cylindrical casing before the partition walls formed at both ends of casing is provided in some cases or the cap is attached. When the casing length of the adsorption column is 500 cm or less, and more preferably 50 cm or less, the porous fiber will be easily inserted into the adsorption column, and the handling in actual use as the adsorption column will tend to be easy. When the casing length is 1 cm or more, and more preferably 3 cm or more, for example, the column tends to be advantageous in the formation of the partition walls formed at both ends of casing, and the handleability of the adsorption column tends to be good.

The shape of the porous fiber when incorporated in the adsorption column is preferably a straight shape, and the fiber having a straight shape is preferably inserted in parallel with the longitudinal direction of the adsorption column case. By the porous fiber having a straight shape, the flow path of the fluid that is to be treated is easily secured, the fluid that is to be treated is evenly distributed inside the adsorption column, and the resistance in the flow path can be easily suppressed. The porous fiber having a straight shape is also advantageous for the increase in pressure loss due to the attachment of solutes and the like. Thus, even when the fluid that is to be treated is blood having a high viscosity, the risk of coagulation or the like in the casing can be easily reduced. The porous fiber can also be processed into a knit, a woven fabric, a nonwoven fabric and the like. However, because a large tension is applied to the yarn during processing, there is a limitation that the proportion of fine pores of the porous fiber should not be high. Further, processing of the porous fiber may lead to an increase in the number of processes and the cost.

The number of the yarn of the porous fiber incorporated in the adsorption column of the present invention is preferably about 1,000 to 500,000.

The upper limit of the packing rate of the porous fiber in the casing of the adsorption column is preferably 70%, and more preferably 63%. The lower limit of the packing rate of the porous fiber is preferably 13%, further preferably 30%, and particularly preferably 45%. When the packing rate of the porous fiber is 13% or more, the amount of blood required for blood purification is reduced, and the burden on the patient can be easily reduced. When the packing rate of the porous fiber is 70% or less, the air releasability tends to be good. Further, the porous fiber can be easily filled, and thus the working efficiency can be easily improved. The "packing rate" as used herein refers to the rate of the volume of the porous fiber in the volume of the casing having an inlet into which the blood flow before purification flows and an outlet from which the blood flow after purification is discharged, and the header and the like are excluded.

The packing rate is the rate of the fiber volume (Vf) calculated from the cross section of the fiber, the length of the casing, and the number of the fibers to the casing volume (Vc) calculated from the cross section and the length of the casing, and is calculated as follows.

$Vc$ (cm$^3$)=cross section of casing body (cm$^2$)×effective length (cm)

$Vf$ (cm$^3$)=cross section of fiver (cm$^2$)×number of fibers×effective length (cm)

Packing rate=$Vf$ (cm$^3$)/$Vc$ (cm$^3$)×100(%)

When the casing has a taper, the cross section of the casing body is defined as the cross section in the middle of the casing.

The Vc as used herein does not include the volumes of members not containing the porous fiber, for example, a member of an inlet and outlet port of the fluid that is to be treated, such as a member called a header or a header cap. When a spacer fiber for preventing the close contact between porous fibers inside the case is used, the Vf includes the volume of the spacer fiber. The effective length of the porous fiber refers to the length obtained by subtracting the length of the partition walls formed at both ends of casing from the length of the casing. The upper limit of the effective length of the porous fiber is preferably 5000 mm, more preferably 500 mm, and particularly preferably 210 mm from the viewpoint of the prevention of fiber bending, easy reduction of pressure loss after formed into a column, and the like. The lower limit of the effective length of the porous fiber is preferably 5 mm, more preferably 20 mm, and particularly preferably 30 mm from the viewpoint that the amount of the yarn discarded can be reduced when, for example, the extra yarn that protrudes from the adsorption column is cut to make the yarn length uniform, productivity tends to be improved, and the handling of the fiber bundle tends to be easy. The measuring method of the effective length of the fiber is as follows: in the case of a crimped yarn, the length of the yarn is measured in a state in which the yarn is stretched from both ends of the yarn and straightened. Specifically, one end of a fiber taken out from the adsorption column is fixed with tape and the like, the fiber is suspended vertically, and the other end is given a weight of about 8 g per cross section (mm$^2$) of the yarn, and the total length when the fiber becomes linear is immediately measured. This measurement is performed on 30 fibers randomly selected from the adsorption column or the like, and the average of the 30 fibers is calculated in units of millimeters and rounded off to the nearest integer.

When the porous fiber is used in a medical device and the like, the porous fiber is preferably disinfected or sterilized before use. Examples of the disinfection and sterilization method include various disinfection and sterilization methods, such as high-pressure steam sterilization, gamma ray sterilization, ethylene oxide gas sterilization, drug disinfection, and ultraviolet ray disinfection. Among these methods, gamma ray sterilization, high-pressure steam sterilization, and ethylene oxide gas sterilization are preferable because they have less effect on sterilization efficiency and materials.

The adsorption column in the present invention also has various uses, and can be used in uses such as water treatment, purification, and blood purification. In the case of the blood purification use, treatment methods include a method in which whole blood is directly perfused and a method in which plasma is separated from blood and then the plasma is passed through the adsorption column. The adsorption column of the present invention can be used in both methods.

When the adsorption column is used as a blood purifier, a method in which the adsorption column is incorporated into an extracorporeal circulation, and adsorption and removal is performed on line is preferable from the viewpoint of the throughput at a time, the simple operation and the like. In this case, the adsorption column of the present invention can be used alone, or can be used with connected in tandem with an artificial kidney during dialysis or the like. By such a method, substances which cannot be sufficiently removed by an artificial kidney only can be removed simultaneously with the dialysis. In particular, the function of the artificial kidney can be complemented by adsorbing and removing inorganic phosphorus and β2MG that are insufficiently removed by an artificial kidney using the adsorption column according to the present invention.

When the adsorption column is used simultaneously with an artificial kidney, the adsorption column can be connected before or after the artificial kidney in the circuit. The advantage of being connected before the artificial kidney is that the original capability of the adsorption column can be easily exhibited because the adsorption column is less likely to be affected by dialysis with the artificial kidney. Meanwhile, advantage of being connected after the artificial kidney is that the solute concentration is high, and an increase in the adsorption and removal efficiency of inorganic phosphorus can be expected because the blood and the like after the water removal by an artificial kidney is treated.

Spinnability was evaluated as follows:
1. When continuous spinning of 5 hours is performed, no yarn breakage occurs during the spinning, and thus spinnability is extremely good.
2. When continuous spinning of 5 hours is performed, more than three yarn breakage occurs during the spinning or the nozzle pressure becomes 20 kPa or more, and thus the spinnability is extremely poor.

[Blood Purification System]

The blood purification system of the present invention is a blood purification system including the adsorption column of the present invention and a water removal column, wherein the adsorption column and the water removal column are connected.

In the blood purification system of the present invention, the adsorption column of the present invention and the water removal column can be connected in tandem for extracorporeal circulation. The water removal column is a column for removing water in blood, and an artificial kidney can be used as the water removal column. In this case, in the B side, the inner side of a hollow fiber, blood flows in the same manner as in dialysis, but in the D side, the outer side of the hollow fiber, blood does not flows, and water is removed by filtration. By using such a method, water and waste products other than water can be removed similarly to dialysis without using dialysate. In artificial dialysis, waste products are removed on the diffusion principle, while in the present invention, water is removed by filtration and waste products other than water are removed by adsorption.

Though in the current artificial dialysis, dialysate of 100 L or more needs to be used at a time, in the present method, the same effect as in artificial dialysis can be expected without using dialysate.

The upper limit of the blood volume of the artificial kidney used for water removal is preferably 60 mL, more preferably 50 mL, and particularly preferably 40 mL, and the lower limit thereof is preferably 10 mL, more preferably 20 mL, and particularly preferably 30 mL. When the blood volume is large, the decrease in blood pressure may occur because the amount of blood taken out from the body at a time is large. Meanwhile, when the blood volume is small, the water removal effect may not be sufficiently achieved.

A hollow yarn is incorporated in the water removal column, the material of the hollow yarn is not particularly limited, and examples of the material that can be used include polymethyl methacrylate, polyacrylonitrile, polysulfone, polyethersulfone, polyarylethersulfone, polypropylene, polystyrene, polycarbonate, cellulose, cellulose triacetate, and ethylene-vinyl alcohol copolymer, which are already clinically used.

EXAMPLES

Hereinafter, the present invention will be described with Examples.

In Examples, various types of particles were used as the granular material. For the substance to be removed, inorganic phosphorus was selected as a model substance of the low molecular weight compound, and β2MG was selected as a model substance of the high molecular weight compound. However, the present invention is not limited by these examples.

Examples 1 to 2

<Preparation of Spinning Solution for Core Liquid>

First, a spinning solution of 21% by mass of PMMA was prepared. Syndiotactic-PMMA (31.7 parts by mass) (syn-PMMA, manufactured by MITSUBISHI RAYON CO., LTD., "Dianal" BR-85) having a mass average molecular weight of 400,000, syn-PMMA (31.7 parts by mass) (manufactured by Sumitomo Chemical Co., Ltd., "Sumipex" AK-150) having a mass average molecular weight of 1,400,000, isotactic-PMMA (16.7 parts by mass) (iso-PMMA, manufactured by TORAY INDUSTRIES, INC.) having a mass average molecular weight of 500,000, and a PMMA copolymer (20 parts by mass) (manufactured by TORAY INDUSTRIES, INC.) having a molecular weight of 300,000 and containing 1.5 mol % of sodium parastyrene sulfonate were mixed with dimethyl sulfoxide (DMSO) (376 parts by mass) and the mixture was stirred at 110° C. for 8 hours to prepare a spinning solution.

In Example 1, to 476 g of the spinning solution obtained above, 190 g of dimethyl sulfoxide and 100 g of titanium oxide particles that act as a phosphorus adsorbent as a granular material were added to prepare a titanium oxide/PMMA spinning solution containing 50% by mass of the granular material, and the spinning solution was stirred at 110° C. for 5 hours to obtain a core liquid. The viscosity of the obtained spinning solution was 750 poise.

Meanwhile, in Example 2, to 476 g of the spinning solution obtained above, 50 g of neodymium carbonate that act as a phosphorus adsorbent as a granular material was added to prepare a neodymium carbonate/PMMA spinning solution containing 50% by mass of the granular material, and the spinning solution was stirred at 110° C. for 5 hours to obtain a core liquid. The viscosity of the obtained spinning solution was 1200 poise.

<Preparation of Spinning Solution for Sheath Liquid> syn-PMMA (32.4 parts by mass) having a mass average molecular weight of 400,000, syn-PMMA (32.4 parts by mass) having a mass average molecular weight of 1,400,000, and iso-PMMA (16.7 parts by mass) having a mass average molecular weight of 500,000 were mixed with 355 parts by weight of dimethyl sulfoxide, and the mixture was stirred at 110° C. for 8 hours to prepare a spinning solution. The viscosity of the obtained spinning solution was 2650 poise.

<Spinning>

An annular slit type spinneret having an outer diameter/inner diameter of 2.0/1.95 mmφ was used. The spinneret was heated to 100° C., the sheath liquid was discharged from the slit at a rate of 0.673 g/min, and the core liquid was discharged from the central part at a rate of 0.735 g/min. The discharged spinning solution was run 500 mm in the air, and then led into a coagulating bath. Water was used for the coagulating bath, and the water temperature (the coagulating bath temperature) was 42° C. The yarn was washed in a water washing bath, led to a bath containing an aqueous solution containing 70% by mass of glycerin as a humectant, then passed through a heat treatment bath at a temperature of 84° C., and wound into a spool at 16 m/min.

The obtained porous fiber having a core-sheath structure was washed, then the washing solution was completely replaced with pure water, the fiber was sandwiched between a slide glass and a cover glass, the outer diameter (the diameter of the outermost periphery) of the yarn was measured at any two points per yarn using a projector (for example, V-10A manufactured by Nikon Corporation), and the average was calculated and rounded off to the nearest integer to obtain the yarn diameter.

Comparative Example 1

Spinning was performed with the same composition of the spinning solution and spinneret as in Example 1. At that time, the discharge rate of the sheath discharged from the slit of the spinneret was 0 g/min.

Comparative Example 2

Spinning was performed with the same composition of the spinning solution and spinneret as in Example 2. At that time, the discharge rate of the sheath discharged from the slit of the spinneret was 0 g/min.

Comparative Example 3

Nylon, a non-porous fiber, was used instead of the porous fiber.

The evaluation results of the adsorption capability for inorganic phosphorus and β2MG of the porous fibers and non-porous fiber of Examples 1 to 2 and Comparative Examples 1 to 3 are shown in Tables 1 and 2.

<Measuring Method>

(1) Method of Preparing the Fluid that is to be Treated

The fluid that is to be treated was prepared by treating bovine blood as follows.

First, bovine blood obtained by adding 15 mL of citric acid (ACD-A solution from Terumo Corporation) to 100 mL of bovine blood was centrifuged at 3000 rpm for 30 minutes to obtain bovine plasma. The bovine plasma was adjusted so that the bovine plasma had a total amount of protein (TP) of 6.5±0.5 g/dL. The bovine plasma used was one within 5 days after blood collection.

Next, 7.85 mg of sodium monohydrogen phosphate ($Na_2HPO_4$) and 3.45 mg of potassium dihydrogen phosphate ($KH_2PO_4$) were added to the bovine plasma so that the concentration of inorganic phosphorus was 6 mg/dL per 100 mL of the bovine plasma.

Further, β2MG was added so that the concentration of β2MG was 1 mg/L per 100 mL of the bovine plasma, thereby the fluid that is to be treated was obtained.

The concentration of inorganic phosphorus in the fluid that is to be treated was measured by the following method. That is, 200 μL of the fluid that is to be treated was stored in a freezer at −20° C. or less, then sent to Nagahama Life Science Laboratory of Oriental Yeast Co., ltd., the concentration of inorganic phosphorus was measured by an enzymatic method in which Determiner L IPII is used, and taken as C1 (mg/dL).

Meanwhile, the concentration of β2MG in the fluid that is to be treated was measured by the following method. That is, 1 mL of the fluid that is to be treated was stored in a freezer at −20° C. or less, then sent to SRL, Inc., the concentration of β2MG was measured by latex agglutination, and taken as C2 (mg/mL).

(2) Adsorption Capability

The porous fibers obtained in Examples 1 and 2 and Comparative Examples 1 and 2, and the nylon obtained in Comparative Example 3 were cut into bundles of 8 cm in length, and placed in a 15 mL centrifuge tube manufactured by Greiner Bio-One so that the volume of the fibers was 0.0905 $cm^3$. The fluid that is to be treated above (12 mL) was placed thereto, and was stirred at room temperature (20 to 25° C.) for 1 hour using a seesaw shaker and the like, for example, Wave-SI manufactured by TAITEC CORPORATION in this Example, set at scale 38 and the maximum angle (one reciprocation in 1.7 seconds). In order to measure the concentration of inorganic phosphorus, C3 (mg/dL) and the concentration of β2MG, C4 (mg/mL) after stirring, 1.5 ml was each sampled, centrifuged at 9000 rpm for 5 minutes, and the supernatant was collected. Before and after stirring, the sample was stored in a freezer at −20° C. or less. For the concentration of inorganic phosphorus, the sample was sent to Nagahama Life Science Laboratory of Oriental Yeast Co., ltd., and the concentration of inorganic phosphorus in supernatant was measured. For the concentration of β2MG, the sample was sent to SRL, Inc., the concentration of β1MG was measured by latex agglutination, and the adsorption amount of inorganic phosphorus per fiber volume was calculated from Formula 4, and the adsorption amount of β2MG per fiber surface area was calculated from Formula 5.

Adsorption amount per fiber volume [mg/g]=[(C1−C2)×0.12 (dL)]/total volume of porous fiber ($cm^3$)　　　Formula 4

Adsorption amount per fiber surface area (βg/$cm^2$)= (C3−C4)×12/total surface area of fiber ($cm^2$)× 1000 porous fibers　　　Formula 5

(3) Measurement of Elution Amount of Granular Material

The porous fibers obtained in Examples 1 and 2 and Comparative Examples 1 and 2, and the nylon obtained in Comparative Example 3 were cut to a length of 10 cm, 250 fibers were placed in a 50 mL centrifuge tube manufactured by Greiner Bio-One, and washed with 40 mL of Otsuka water for injection five times, and the washing solution of the fifth washing was sampled and taken as the eluate before stirring (N1). Then, another 40 mL of water for injection was added thereto, the mixture was stirred at room temperature (20 to 25° C.) for 1 hour using a seesaw shaker and the like, for example, Wave-SI manufactured by TAITEC CORPORATION set at scale 38 and the maximum angle (one reciprocation in 1.7 seconds), and taken as the eluate after stirring (N2). The washing solution and the eluate were subjected to measurement with a fine particle counter (KL-04 manufactured by RION Co., Ltd.), and the number of granular material fine particles eluted was calculated from Formula 6.

Number of eluted fine particles=N2−N1　　　Formula 6

(4) Measurement of Yarn Diameter

The fiber was sandwiched between a slide glass and a cover glass, and the fiber diameter was measured using V-10 manufactured by Nikon Corporation.

(5) Average Pore Size

The average pore size was measured with a differential scanning calorimeter (DSC).

(6) Area Occupancy Rate of Granular Material

The area occupancy rate was measured and calculated with an electron microscope (SEM) (manufactured by Hitachi High-Technologies Corporation, S-5500), as described above.

Example 3

<Preparation of Adsorption Column>

A plurality of porous fibers obtained in Example 1 was packed in a polycarbonate cylindrical casing having an inner diameter of 10 mm and an axial length of 17.8 mm.

More specifically, 655 in total of the yarn having a yarn diameter of 290 μm obtained in Example 1 cut to a length of 17.8 mm were packed in a column to obtain a column having a packing rate of 55.1%. Next, a polypropylene mesh filter having an aperture equivalent diameter of 84 μm and an opening ratio of 36% which was cut to the same diameter as the inner diameter of the casing was attached to the flow inlet and outlet port of the fluid that is to be treated in edge faces on both sides. Finally, a cap called a header having a flow inlet and a flow outlet of the fluid that is to be treated was attached to the end of the casing to obtain an adsorption column. The obtained adsorption column was evaluated based on the following <Measurement of phosphorus adsorption capability of adsorption column>. The results are shown in Table 3.

Example 4

Into the same adsorption column as in Example 3, 760 in total of the yarn having a yarn diameter of 170 μm obtained in Example 2 cut to a length of 17.8 mm were packed to obtain an adsorption column having a packing rate of 22.2%. The obtained adsorption column was evaluated based on the following <Measurement of phosphorus adsorption capability of adsorption column>. The results are shown in Table 3.

<Measurement of Phosphorus Adsorption Capability of Adsorption Column>

For the evaluation of the adsorption capability, the phosphorus adsorption capability of the adsorption column was measured. Bovine plasma was obtained in the same manner as in the evaluation of the adsorption capability in Examples 1 and 2 and Comparative Examples 1 to 3 mentioned above. The bovine plasma was adjusted so that the bovine plasma had a total amount of protein of 6.5±0.5 g/dL. The bovine plasma used was one within 5 days after blood collection. Next, 7.85 mg of sodium monohydrogen phosphate ($Na_2HPO_4$) and 3.45 mg of potassium dihydrogen phosphate ($KH_2PO_4$) were dissolved in 100 mL of the bovine plasma above to prepare the fluid that is to be treated that mimics hyperphosphatemia.

A silicone tube was attached to the inlet and outlet of the adsorption column, and both the inlet and outlet were immersed in the fluid that is to be treated to form a circulatory system. The fluid that is to be treated was flowed at a flow rate of 2.5 mL/min, passed through the adsorption column from the inlet of the adsorption column, and then the purified fluid was returned to the fluid that is to be treated from the outlet. The fluid that is to be treated and the purified fluid at the outlet were sampled, and the concentration of inorganic phosphorus in the sample was measured.

TABLE 2

|  | Elution amount of fine particles (number/mL) | Phosphorus adsorption capability (mg/cm³) | β2MG adsorption capability (μg/cm³) | Spinnability |
|---|---|---|---|---|
| Example 1 | 30 | 2.5 | 8.5 | 1 |
| Example 2 | 20 | 9.6 | 6.4 | 1 |
| Comparative Example 1 | 160 | 5.9 | 2.8 | 2 |
| Comparative Example 2 | 141 | 11.5 | 3.8 | 2 |
| Comparative Example 3 | — | 0.1 | 0.9 | — |

TABLE 3

|  | Granular material | Phosphorus adsorption capability of column (mg/cm³) | Fiber diameter (μm) | Average radius of pore (nm) | Specific surface area of pore (m²/g) |
|---|---|---|---|---|---|
| Example 3 | Titanium oxide | 2.4 | 171 | 15 | 66 |
| Example 4 | Neodymium carbonate | 4.7 | 290 | — | — |

The invention claimed is:

1. A porous fiber, comprising a three-dimensional pore structure formed by a fiber having a solid shape, wherein the three-dimensional pore structure has an average radius of pores in a range of 0.5 nm or more and 100 nm or less,
wherein the fiber having a solid shape has a yarn diameter in a range of 20 μm or more and 1000 μm or less,
wherein the porous fiber satisfies all requirements below:
(1) having a granular material having a particle diameter of 200 μm or less, and having an area occupancy rate of the granular material having a particle diameter of 200 μm or less, in a cross section of the three-dimensional pore structure, of 3.0% or more; and
(2) not having the granular material having a particle diameter of 200 μm or less in a region within 1.0 μm in a depth direction from an outermost surface.

2. The porous fiber according to claim 1, having a surface porosity in a range of 0.5% or more and 30.0% or less.

3. The porous fiber according to claim 1, wherein the three-dimensional pore structure has a specific surface area of pores of 10 m²/g or more.

TABLE 1

|  | Granular material | Polymer | Yarn diameter (μm) | Particle diameter of granular material (μm) | Area occupancy rate (%) | Rate of granular material within 1 μm in depth (%) | Average radius of pore (nm) | Specific surface area of pore (m²/g) | pH change | Surface porosity (%) |
|---|---|---|---|---|---|---|---|---|---|---|
| Example 1 | Titanium oxide | PMMA | 171 | 12 | 12 | 0 | 13 | 350 | 0.2 | 5.13 |
| Example 2 | Neodymium carbonate | PMMA | 290 | 31 | 10 | 0 | ND | ND | 0.3 | 4.70 |
| Comparative Example 1 | Titanium oxide | PMMA | 121 | 12 | 20 | 5 | 11 | 306 | 0.2 | 7.21 |
| Comparative Example 2 | Neodymium carbonate | PMMA | 166 | 31 | 16 | 3 | — | — | 0.3 | 6.12 |
| Comparative Example 3 | — | Nylon | 120 | — | 0 | 0 | — | — | 0 | — |

4. The porous fiber according to claim 1, having a core-sheath structure or a sea-island structure.

5. The porous fiber according to claim 1, wherein the granular material is inorganic particles.

6. The porous fiber according to claim 1, wherein the granular material includes at least one selected from the group consisting of active carbon, carbon nanotube, graphene, graphite, and graphene oxide.

7. The porous fiber according to claim 1, wherein the granular material selectively adsorbs a low molecular weight compound having a molecular weight of less than 1000.

8. The porous fiber according to claim 1, wherein the granular material is inorganic particles and has phosphorus adsorption capability.

9. The porous fiber according to claim 1, wherein a pore in the three-dimensional pore structure selectively adsorbs a high molecular weight compound having a molecular weight of 1000 or more.

10. The porous fiber according to claim 1, comprising polymethyl methacrylate.

11. The porous fiber according to claim 1, wherein a pH change of a sample of physiological saline is −1 or more and +1 or less, wherein the pH change is the difference between the pHs before and after the porous fiber is put in the physiological saline and stirred at 200 rpm for 4 hours.

12. The porous fiber according to claim 1, which is used for medical use.

13. An adsorption column, comprising the porous fiber according to claim 1 packed into the adsorption column.

14. A blood purification system, comprising:
the adsorption column according to claim 13; and
a water removal column, wherein
the adsorption column and the water removal column are connected.

* * * * *